United States Patent [19]

McAleer et al.

[11] Patent Number: 4,617,260
[45] Date of Patent: Oct. 14, 1986

[54] RIA ASSAY FOR HBCAG

[75] Inventors: William J. McAleer, Ambler; William J. Miller, North Wales, both of Pa.

[73] Assignee: Merck & Co., Inc., Rahway, N.J.

[21] Appl. No.: 238,780

[22] Filed: Feb. 27, 1981

[51] Int. Cl.$^4$ .................. G01N 53/00; G01N 33/545; C12Q 1/70
[52] U.S. Cl. .......................................... 435/5; 435/7; 435/235; 435/948; 436/518; 436/531; 436/533; 436/547; 436/804; 436/811; 436/820; 436/823
[58] Field of Search .................. 424/1, 1.5, 89, 1.1; 435/7, 5, 4, 235–239; 436/518–523, 528–535, 547, 804, 811, 815, 820, 823, 825

[56] References Cited

U.S. PATENT DOCUMENTS

| | | | |
|---|---|---|---|
| 4,038,378 | 7/1977 | Khare | 436/523 |
| 4,118,479 | 10/1978 | Prince et al. | 424/89 |
| 4,189,464 | 2/1980 | Blumberg et al. | 424/1 |
| 4,241,175 | 12/1980 | Miller et al. | 435/7 |
| 4,248,965 | 2/1981 | Mochida et al. | 435/7 |
| 4,267,270 | 5/1981 | Stout | 435/7 |

OTHER PUBLICATIONS

Chiang et al, Shang-hai I Hsueh, vol. 2(8), pp. 47–49, 1979.
Miles, L. E. M., Ricerca in Clinicae in Laboratorio, vol. 5, pp. 59–72 (1975), (Properties, Variants . . . ).
Purcell, R. H. et al, Journal of Immunology, vol. 116(2), pp. 349–356 (1976).
Neurath, A. R. et al, J. General Virology, vol. 38, pp. 549–559 (1978).
Purcell, R. H. et al, Intervirology, vol. 2, pp. 231–243, (1973/1974).
Purcell, R. H. et al, The Lancet, pp. 757–761 (Oct. 9, 1976).
Purcell, R. H. et al, Applied Microbiology, vol. 26(4), pp. 478–484 (1976).

*Primary Examiner*—Thomas G. Wiseman
*Assistant Examiner*—M. Moskowitz
*Attorney, Agent, or Firm*—Donald J. Perrella; Hesna J. Pfeiffer

[57] ABSTRACT

HBcAb in a biological fluid is adsorbed on a surface which is then coated with BSA. The coated surface is then incubated first in the sample and then in the presence of radiolabelled HBcAb.

8 Claims, No Drawings

RIA ASSAY FOR HBCAG

BACKGROUND OF THE INVENTION

Prior art methods for detecting hepatitis B core antigen (HBcAg) involved the use of immune adherence hemagglutination assay (IAHA) or complement fixation (CF) assay. A disadvantage of such assays is that the end-point determination requires interpretation of observed results and therefore is necessarily subjective to some degree. These assays are not sufficiently sensitive for routine use to detect the presence of HBcAg in biological fluids, expecially sera or plasma, in order to prevent transmission of hepatitis B disease by transfusion and also to diagnose the presence of this disease in a person.

OBJECTS OF THE INVENTION

It is an object of the present invention to provide an improved assay for HBcAg. Another object is to provide an assay which is more sensitive than the IAHA or CF assays. A further object is to provide an assay having an objective, that is, a non-interpretive, end point determination. These and other objects of the present invention will be apparent from the following description.

SUMMARY OF THE INVENTION

HBcAb in a biological fluid is adsorbed on a surface which is then coated with BSA. The coated surface is then incubated first in the sample and then in the presence of radiolabelled HBcAb.

DETAILED DESCRIPTION

The present invention relates to an RIA assay for HBcAg and, more particularly to a two-part RIA assay for HBcAg.

The starting material for the assay of the present invention is plasma which contains hepatitis B core antibody (HBcAb). Such plasma can be located by screening plasma from donors who are positive for hepatitis B surface antigen (HBsAg) using a suitable assay, e.g., IAHA, to detect HBcAb. The plasma should have an IAHA titer of HBcAb of about 1:2000 or higher, or an equivalent quantity if measured by another assay. Preferably the plasma has an IAHA titer of HBcAb of about 1:20,000 or higher. The plasma is then treated, e.g., by centrifugation to obtain a fraction negative for HBsAg but positive for HBcAb. This plasma fraction is then treated to isolate gamma globulin proteins including HBcAb, for example, by adding $(NH_4)_2SO_4$ to the plasma fraction to precipitate gamma globulin proteins. The isolated gamma globulin proteins are then fractionated, e.g., chromatographically, and the fraction containing HBcAb is collected and radioiodinated in known manner.

An additional quantity of the plasma fraction which is negative for HBsAg but positive for HBcAb is used to coat a suitable substrate, e.g., a plastic sphere. The substrate is then incubated with a material adapted to occupy substantially all remaining sites available for non specific adsorption. An example of such a material is bovine serum albumin (BSA). A sample to be tested for presence of HBcAg is incubated with the coated substrate. A similar sample but which is known to be free of HBcAg (negative control) also is incubated with the coated substrate, as also is a solution known to contain HBcAg (positive control). The presence of HBcAg in the sample, if any, is then determined quantitatively by adding some of the HBcAb iodination product to each incubation and counting the resulting radioactivity.

This assay can be used for the detection of hepatitis B virus replication in cell culture and is a definitive test for clinical infection. It is especially useful under circumstances when other markers such as surface antigen may not be expressed.

The following examples illustrate the present invention without, however, limiting the same thereto.

EXAMPLE 1

Step A

HBcAb is detected in the plasma of HBsAg-positive donors by screening using the immune adherence hemagglutination assay (IAHA). Plasma is selected from a donor having a titer of 1:32,000. A quantity of the plasma, 4 ml, is centrifuged over 1 ml of a 25% (wt/wt) sucrose solution at 360,000×g for 3 hours. The top 3 ml of the supernatant liquid is aspirated and tested for the presence of both HBsAg by complement fixation and for HBcAb by IAHA. The liquid is negative for HBsAg and has a HBcAb titer of 1:32,000. To 1 ml of the supernatant liquid there are added 202 mg of $(NH_4)_2SO_4$ with mixing to effect dissolution. The resulting solution is held for 18 hours at 5° C. and then centrifuged at 2,000×g for 1 hour. The pellet is resuspended in 1 ml of cold phosphate buffered saline (PBS) containing 202 mg of $(NH_4)_2SO_4$ and centrifuged as before. The pellet is dissolved in 1 ml of 0.01M phosphate buffer, pH 8.1. The buffer solution is applied to a 13 ml column of diethylaminoethyl dextran (DEAE Sephadex A-25) and eluted with the same buffer. The gamma globulin fraction in the eluate is located by IAHA for HBcAb. It has a HBcAb titer of 1:8,000 and a protein concentration of 4 mg/ml. This globulin (50 μg) is radioiodinated with $^{125}I$ using the chloramine T method described by Hunter et al., Nature, 194:495–496 (1962). The iodination product is separated from free iodine by gel filtration and diluted in 100 ml of PBS containing 50% fetal calf serum and 0.02% $NaN_3$. The diluted material contains 35,172 counts/minute per 10 μliters.

Step B

A quantity, 1 ml, of the supernatant liquid obtained by centrifuging the plasma at 360,000×g is diluted 1:100 in PBS and is used to coat about 250 polystyrene plastic spheres (0.64 cm diameter) having a roughened surface. The spheres are stored overnight at 5° C. to effect the coating. The coating solution is then discarded and the spheres are washed with 4×1 liter of PBS. The beads are incubated overnight in 100 ml of a 1 mg/ml solution of BSA in PBS. The incubating solution is then discarded and the beads washed again with 4×1 liter of PBS and finally with 1 liter of distilled water. The beads are air dried at room temperature for 6 hours and then held at −20° C.

A sample (0.2 ml) of sonicated cell culture of hepatitis B infected chimpanzee liver is incubated with a HBcAb coated bead from step B at 25° C. for 16 hours. At the same time a 0.2 ml sample of an uninfected sonicated cell culture of chimpanzee liver is also incubated with each of 5 of the HBcAb coated beads. A known solution containing HBcAg (IAHA titer of 1:2) is also incubated with two of the HBcAb coated beads as positive controls. At the end of the incubation period, the beads are washed two times in 5 ml of distilled water.

A quantity of the iodination product from Step A, 0.2 ml, is added to each of the beads in the test. After incubating at 37° C. for 4 hours, the beads are washed with 2×5 ml portions of distilled water and counted for 1 minute in a gamma counter. The following results are obtained:

| Positive Controls (Mean) | Unknown | Negative Controls (Mean) | Cut-Off |
| --- | --- | --- | --- |
| 22,106 | 1,142 | 412 | 635* |

*Obtained by averaging the 5 negative controls, calculating the standard deviation, and adding 5 standard deviations to the average to obtain a cut-off value of 635 counts/minute. Since the unknown is above 635, the unknown is positive.

A sample of liver is excised from a chimpanzee infected with hepatitis B, finely minced by chopping, washed and planted in cell culture medium (Williams Medium E with 0 to 20% animal serum, $10^{-6}$ M insulin, dexamethasone, and glucagon). Cultures in 25 cm² flasks are refed with 2 to 3 ml of culture media 2 to 3 times per week. Incubation is at 35° C. on a rocker platform in a gas atmosphere of air and 5% $CO_2$. Within 7 days a vigorous outgrowth of hepatocyte-like epithelial cells begins.

Another sample of liver excised from a chimpanzee free of hepatitis B infection is treated similarly.

A sample from each tissue culture is sonicated separately and treated as in Example 1. The sample grown from the chimpanzee infected with hepatitis B is positive for HBcAg; the sample grown from the chimpanzee free of hepatitis B infection is negative for HBcAg.

EXAMPLE 3

A tissue culture is grown from a human hepatoma cell line which sheds HBsAg (Alexander cells, American Type Culture Collection accession number CCL 8024). A sample from the tissue culture is sonicated and treated as in Example 1. It is negative for the presence of HBcAg.

EXAMPLE 4

The procedure of Example 3 is repeated using a biopsy sample from normal human liver. It is negative for the presence of HBcAg.

EXAMPLE 5

The procedure of Example 3 is repeated using a tissue culture of WI-38 cells (ATCC CCL-75). It is negative for the presence of HBcAg.

EXAMPLE 6

The procedure of Example 1, Step B, is repeated using samples from several lots of human plasma. Each sample is tested separately. Some of the lots are found to be positive for the presence of HBcAg and are rejected for use in human patients in need of plasma.

What is claimed is:

1. A method for detecting HBcAg in a biological fluid which comprises:
   contacting a plasma fraction having an amount of antibody which binds to HBcAg sufficient to permit detection of HBcAg in a biological fluid by immunoradiometric assay but having no detectible HBsAg with a suitable support under conditions sufficient to coat said support with said plasma fraction contacting said HBsAg-free plasma-fraction-coated support with a proteinaceous material under conditions such that substantially all areas of the support not coated with said HBsAg-free plasma fraction are coated with said proteinaceous material to minimize non-specific adsorption incubating said coated support with the biological fluid under conditions such that any HBcAg in said biological fluid binds to said support washing said coated support incubating said washed coated support with a radiolabelled plasma fraction, having an amount of antibody which binds to HBcAg sufficient to permit detection of HBcAg in a biological fluid by immunoradiometric assay but having no detectible HBsAg under conditions such that the radiolabelled plasma fraction binds to the washed support and measuring the radioactivity bound to the support.

2. A method according to claim 1 wherein the suitable substrate is a plastic.

3. A method according to claim 2 wherein the plastic is substantially spherical in shape.

4. A method according to claim 2 wherein the plastic is polystyrene.

5. A method according to claim 2 wherein the plastic is polystyrene having a substantially spherical shape.

6. A method according to claim 1 wherein the radiolabelled plasma fraction is labelled with $^{125}I$.

7. A method according to claim 1 wherein the plasma has an HBcAb titer of at least about 1:20,000.

8. A method according to claim 1, wherein the radiolabelled plasma fraction is obtained by isolating from the plasma a fraction which is negative for HBsAg but positive for HBcAb, and isolating gamma globulin proteins from the fraction.

* * * * *